(12) United States Patent
Jayaraman (10) Patent No.: US 8,118,987 B2
(45) Date of Patent: Feb. 21, 2012

(54) TWO-DIMENSIONAL CONTROL OF ELECTROCHEMICAL SURFACE POTENTIALS

(75) Inventor: Shrisudersan Jayaraman, Painted Post, NY (US)

(73) Assignee: Corning Incorporated, Corning, NY (US)

(*) Notice: Subject to any disclaimer, the term of this patent is extended or adjusted under 35 U.S.C. 154(b) by 1210 days.

(21) Appl. No.: 11/897,109

(22) Filed: Aug. 29, 2007

(65) Prior Publication Data

US 2009/0057152 A1    Mar. 5, 2009

(51) Int. Cl.
*B01D 61/42* (2006.01)
*B01D 61/58* (2006.01)

(52) U.S. Cl. ........................................ 204/547
(58) Field of Classification Search .................. 204/451, 204/458, 461, 547
See application file for complete search history.

(56) References Cited

U.S. PATENT DOCUMENTS

| | | | | |
|---|---|---|---|---|
| 2001/0047941 | A1* | 12/2001 | Washizu et al. ............... | 204/547 |
| 2002/0088712 | A1* | 7/2002 | Miles .............................. | 204/643 |
| 2006/0185982 | A1* | 8/2006 | Park et al. ...................... | 204/547 |

OTHER PUBLICATIONS

Jayaraman, S. and A.C. Hillier, Construction and reactivity mapping of a platinum catalyst gradient using scanning electrochemical microscope. Langmuir, 2001. 17(25): p. 7857-7864.
Jayaraman, S. and A.C. Hillier, Construction and reactivity screening of a surface composition gradient for combinatorial discovery of electro-oxidation catalysts. Journal of Combinatorial Chemistry, 2004. 6(1): p. 27-31.
Jayaraman, S. and A.C. Hillier, Electrochemical synthesis and reactivity screening of a ternary composition gradient for combinatorial discovery of fuel cell catalysts. Measurement Science & Technology, 2005. 16(1): p. 5-13.
Wang, X.J., et al. Length scale heterogeneity in lateral gradients of poly(N-isopropylacrylamide) polymer brushes prepared by surface-initiated atom transfer radical polymerization coupled with in-plane electrochemical potential gradients. Langmuir, 2006. 22(2): p. 817-823
Wang, X.J., R.T. Haasch, and P.W. Bohn, Anisotropic hydrogel thickness gradient films derviatized to yield three-dimensional composite materials. Langmuir, 2005. 21(18): p. 8452-8459.
Coleman, B.D., N.-Finnegan, and P.W. Bohn, Sharply defined-lateral composition gradients of copper on-gold by spatiotemporal control of the in-plane electrochemical potential distribution. Thin Solid Films, 2004. 467(1-2): p. 121-126.
Plummer, S.T., et al., Electrochemically derived gradients of the extracellular matrix protein fibronectin on gold. Langmuir, 2003. 19(18): p. 7528-7536.
Balss, K.M., et al., Active spatiotemporal control of electrochemical reactions by coupling to in-plane potential gradients. Journal of Physical Chemistry B, 2001. 105(37): p. 8970-8978.

(Continued)

*Primary Examiner* — Bruce Bell
(74) *Attorney, Agent, or Firm* — Jason A Barron; Joseph M Homa; Siwen Chen (57) ABSTRACT

A method for providing a two dimensional spatially varying surface potential on a surface of a conductive substrate and use thereof. The method comprises providing a conductive substrate having a first conductive surface and comprising an array of "n" electrical potential contact points spatially arranged in two dimensions on the first conductive surface, wherein "n" is at least 3. An electrical potential is then applied to each of the "n" electrical contact points, wherein the electrical potentials applied to at least two of the "n" electrical potential contact points are different. Also disclosed are methods and applications for use of the methods disclosed herein.

19 Claims, 3 Drawing Sheets

OTHER PUBLICATIONS

Jayaraman, S. and A.C. Hillier, Screening the reactivity of PtxRuy and PtxRuyMoz catalysts toward the hydrogen oxidation reaction with the scanning electrochemical microscope. Journal of Physical Chemistry B, 2003. 107(22): p. 5221-5230.

Jayaraman, S. and A.C. Hillier, Combinatorial Synthesis and Reactivity Screening of Electro-oxidation Catalyst Gradients. Materials Research Society Symposium Proceedings, 2004. 804: p. JJ8.11.1-JJ8.11.9.

Colyer, C.L., et al. Clinical potential of microchip capillary electrophoresis systems. Electrophoresis, 1997. 18(10): p. 1733-1741.

Baldwin, R.P., Recent advances in electrochemical detection in capillary electrophoresis. Electrophoresis, 2000. 21(18): p. 4017-4028.

Bruin, G.J.M., Recent developments in electrokinetically driven analysis on microfabricated devices. Electrophoresis, 2000. 21(18): p. 3931-3951.

Chovan, T. and A Guttman, Microfabricated devices in biotechnology and biochemical processing. Trends in Biotechnology, 2002. 20(3): p. 116-122.

Figeys, D., Adapting arrays and lab-on-a-chip technology for proteomics. Proteomics, 2002. 2(4): p. 373-382.

Ng, J.H. and L.L. Ilag, Biomedical applications of protein chips. Journal of Cellular and Molecular Medicine, 2002. 6(3): p. 329-340.

Yang, J., C.W. Li, and M.S. Yang, Lab-on-a-chip (microfluidics) technology. Acta Biochimica Et Biophysica Sinica, 2002. 34(2): p. 117-123.

Andersson, H. and A. van den Berg, Microfluidic devices for cellomics: a review. Sensors and Actuators B, 2003. 92(3): p. 315-325.

Gambari, R., et al., Applications to cancer research of "lab-on-a-chip" devices based on dielectrophoresis (DEP). Technology in Cancer Research & Treatment, 2003. 2(1): p. 31-39.

Sato, K., et al., Microchip-based chemical and biochemical analysis systems. Advanced Drug Delivery Reviews, 2003. 55(3): p. 379-391.

Weigl, B.H., R.L. Bardell, and C.R. Cabrera, Lab-on-a-chip for drug development. Advanced Drug Delivery Reviews, 2003. 55(3): p. 349-377.

Zieziulewicz, T.J., et al., Shrinking the biologic world—Nanobiotechnologies for toxicology. Toxicological Sciences, 2003. 74(2): p. 235-244.

Deisingh, A.K. and M. Thompson, Biosensors for the detection of bacteria. Canadian Journal of Microbiology, 2004. 50(2): p. 69-77.

Liu, S.R. and A. Guttman, Electrophoresis microchips for DNA analysis. Trends in Analytical Chemistry, 2004. 23(6): p. 422-431.

Schasfoort, R.B.M., Proteomics-on-a-chip: the challenge to couple lab-on-a-chip unit operations. Expert Review of Proteomics, 2004. 1(1): p. 123-132.

Doku, G.N., et al., On-microchip multiphase chemistry—a review of Microreactor design principles and reagent contacting modes. Tetrahedron, 2005. 61(11): p. 2733-2742.

Toner, M. and D. Irimia, Blood-on-a-chip. Annual Review of Biomedical Engineering, 2005. 7: p. 77-103.

Madou, M., et al., Lab on a CD. Annual Review of Biomedical Engineering, 2006. 8:p. 601-628.

Parviz, B.A., Integrated electronic detection of biomolecules. Trends in Microbiology, 2006. 14(9): p. 373-375.

Wang, Q. and P.W. Bohn, Surface composition gradients of immobilized cell signaling molecules. Epidermal growth factor on gold. Thin Solid Films, 2006. 513(1-2): p. 338-346.

Wang, X.J., et al., Interfacial free energy gradients and active spatiotemporal control of molecular recognition and binding. Abstracts of Papers of the American Chemical Society, 2005. 230: p. U364-U365.

Plummer, S.T. and P.W. Bohn, Spatial dispersion in electrochemically generated surface composition gradients visualized with covalently bound fluorescent nanospheres. Langmuir, 2002. 18(10): p. 4142-4149.

Jayaraman Shrisudersan et al., "Scanning electrochemical mapping of spatially localized electrochemical reactions induced by surface potential gradients." Langmuir: The ACS Journal of Surfaces and Colloids Dec. 5, 2006, vol. 22, No. 25, pp. 10322-10328.

Coleman B. D. et al., "Factors influencing the interfacial width of copper gradients on gold produced by spatiotemporal control of the in-plane electrochemical potential distribution : electrode geometry and plating solution composition", Journal of Electroanalytical Chemistry and Interfacialelectrochemistry, Elsevier, Amsterdam, NL, vol. 571, No. 2, Oct. 1, 2004, pp. 139-148.

Khire V. S. et al., "Ultrathin gradient films using thiol-ene polymerizations", Journal of Polymer Science, Part A: Polymer Chemistry 20061215 John Wiley and Sons Inc. US, vol. 44, No. 24, pp. 7027-7039.

* cited by examiner

TWO-DIMENSIONAL CONTROL OF ELECTROCHEMICAL SURFACE POTENTIALS

BACKGROUND OF THE INVENTION

1. Field of the Invention

The present invention relates generally to methods for controlling the electrochemical surface potential on a surface and use thereof. In particular, the present invention relates to method for the two-dimensional spatially varying control of the electrical surface potential on the surface of a conducting substrate and method using such control for discovering a target, detecting a target, and systems for implementing such method. The present invention is useful, e.g., for combinatorial catalyst discovery, chemical sensing and biochemical sensing.

2. Technical Background

Electrochemistry is a branch of chemistry that deals, in part, with processes occurring on surfaces (i.e., electrodes) due to interplay between electrical and chemical effects. This field encompasses a variety of phenomena and applications of technological importance including electrocatalysis, corrosion, batteries, fuel cells, double-layer capacitors, electrochemical sensors, electrochemical synthesis, electroplating, electrophoresis, electrochromic displays, etc. In many of these applications, surface processes can be manipulated by controlling the potential or the current of one or more electrodes in the system.

In conventional electrochemical experiments, uniform surface potentials are applied to electrode surfaces. Although there can be non-uniformities in surface potentials due to the electronic resistance of the electrodes, the intent is typically to apply a uniform electrochemical potential across the electrode surface so as to ensure that each and every point on the electrode surface has the same surface energy. Such uniformity can lead to reproducible electrochemical processes across the electrode surface. With the advent of combinatorial materials and methods, such as, for example, drug discovery, conventional approaches to scientific problems have changed to allow greater throughput of experimental samples and faster cycle time for the development of new products. Researchers across a wide variety of fields such as drug discovery, materials research, homogeneous and heterogeneous catalysis, surface chemistry, have adopted combinatorial methods due, in large part, to the ability of combinatorial methods to systematically study the performance of materials as a function of a relevant material or processing parameter in an accelerated fashion. For example, combinatorial methods have enabled catalyst discovery processes to be shortened from several decades to a few days or less. Combinatorial processes typically require both a method to create a spatially varying library of materials and analytical methodologies to screen and map the performance of each library component.

Thus, the ability to control the surface energy of a particular library material (e.g., a substrate) as a function of position can be determinative to the successful outcome of a combinatorial experiment. Such control can be in an array platform or a gradient platform. In an array platform, the surface energy across a surface is controlled by adjusting individual points, whereas in the gradient platform a gradual change in surface energy is achieved by controlling a few specific points. There are several ways one can envision control of surface energy of a particular material, including the control of temperature, local composition of precursor materials, pressure, etc.

Thus, a need exists for improved control of surface energies for combinatorial processes, such as, for example, the creation and control of surface energy gradients across the surface of an electrode. The present invention provides various methods for creating and controlling such a gradient.

SUMMARY OF THE INVENTION

A first aspect of the present invention relates to a method for discovering a target from a plurality of candidates of materials and/or processes, comprising:

(I.1) providing an electrically conductive surface;

(I.2) providing a defined non-linearly spatially varying electric field across the surface;

(I.3) supplying a source material to the surface;

(I.4) causing the source material to undergo an electrochemical process on the surface in the presence of the non-linearly spatially varying electric field, whereby a plurality of candidates are generated;

(I.5) measuring a plurality of candidates on the surface to yield performance data thereof;

(I.6) comparing the performance data of the measured candidates; and (I.7) discovering the target according to the comparison in step (I.6).

In certain embodiments of the method of the first aspect of the present invention, in step (I.5), at least part of the measuring is conducted in-situ while the candidates remain on the surface.

In certain embodiments of the method of the first aspect of the present invention, the surface provided in step (I.1) is a flat surface. In certain other embodiments, the surface is a curved surface such as a spherical, an ellipsoidal, and other curved surface.

In certain embodiments of the method of the first aspect of the present invention, in step (I.1), the electric field is created by providing n (n being a positive integer of at least three) points on the surface with differing electrical potential. In certain specific embodiments, $n \geq 4$; in certain embodiments, $n \geq 8$; in certain other embodiments, $n \geq 16$.

In certain embodiments of the method of the first aspect of the present invention, in step (I.4), at least p (p being a positive integer of at least 100) candidates are generated; and in step (I.5), at least q (q being a positive integer of at least 10 and $q \leq p$) candidates are measured. In certain specific embodiments, $p \geq 1000$, and $q \geq 800$; in certain specific embodiments, $p \geq 1000$, and $q \geq 1000$; in certain other specific embodiments, $p \geq 5000$ and $q \geq 3000$; in certain other specific embodiments, $p \geq 5000$ and $q \geq 5000$; in certain specific embodiments, $p \geq 10000$ and $q \geq 5000$; in certain specific embodiments $p \geq 10000$ and $q \geq 8000$; in certain embodiments $p \geq 10000$ and $q \geq 10000$.

In certain embodiments of the method of the first aspect of the present invention, step (I.5) is at least partly carried out on the surface in the presence of an electric field.

In certain embodiments of the method of the first aspect of the present invention, in step (I.3), the source material is a metal precursor; in step (I.4), the metal precursor is reduced to elemental metal and deposited on the surface to form the plurality of candidate materials; and in step (I.5), the catalytic performance of the candidates are measured.

In certain embodiments of the method of the first aspect of the present invention, the method further comprises a step (I.8) below, which may be implemented prior or subsequent to step (I.7) above:

(I.8) analyzing the composition of the target.

In certain embodiments of the method of the first aspect of the present invention, in step (I.3), a plurality of candidate materials are generated, said candidate materials having an essentially continuous gradient of at least one component thereof across the surface.

A second aspect of the present invention relates to a method for detecting a target substance in a media, comprising: (II.1) providing a surface having thereon a layer of marking molecules sensitive to the target substance; (II.2) forming a defined pattern of the marking molecules by providing a defined non-linearly spatially varying electric field across the surface; (II.3) determining the target area on the surface where the target substance can selectively bind; (II.4) contacting the media with the surface; and (II.5) binding the target substance to the surface and/or the marking molecules at the predetermined target area in the surface.

In certain embodiments of the method of the second aspect of the present invention, in step (II.1), the surface is electrically conductive, and the layer of marking molecules is a self-assembled mono-layer of thiol molecules.

In certain embodiments of the method of the second aspect of the present invention, the method further comprises: (II.6) determining the presence or absence of the target substance at the predetermined target area on the surface.

In certain embodiments of the method of the second aspect of the present invention, in step (II.2), the defined pattern of the marking molecules provide target areas where multiple target substances can separately, simultaneously, selectively bind. In certain specific embodiments, in step (II.5), multiple target substances are bound to the surface and/or the marking molecules at the predetermined target areas.

In certain embodiments of the method of the second aspect of the present invention, in step (II.1), the surface comprises a layer of gold having a thickness equal to or less than 500 nm. In certain embodiments, the marking molecules to be bound with the layer of gold are thiol molecules.

A third aspect of the present invention relates to a method for detecting the presence and/or concentration of a target substance in a media, comprising: (III.1) providing an electrically conductive surface; (III.2) providing a defined non-linearly spatially varying electric field across the surface; (III.3) contacting the media with the surface; (III.4) causing the target substance, if any, to undergo an electrochemical reaction on the surface in the presence of the electric field; and (III.5) determining the presence of the target substance by detecting the occurrence of the electrochemical reaction; and (III.6) optionally determining the concentration of the target substance in the media according to the location of the reaction.

In certain embodiments of the method of the third aspect of the present invention, the method further comprises the following step (III.7):

(III.7) correlating the location of the electrochemical reaction to the presence and/or concentration of a target substance in the media.

A fourth aspect of the present invention relates to a system for discovering a target from a plurality of candidates of materials and/or processes, comprising:

(IVA) a substrate having a surface on which: (i) a defined non-linearly spatially varying electric field can be established; (ii) a source material can be supplied; and (iii) the source material can undergo an electrochemical process in the presence of the electric field to generate a plurality of candidates; and (IVB) a measuring device for measuring the performance of the candidates.

In certain embodiments of the system according to the fourth aspect of the present invention, the candidates are material candidates, and the system further comprises:

(IVC) an analyzing device for determining the composition of a candidate.

In certain embodiments of the system according to the fourth aspect of the present invention, the substrate (IVA) and the measuring device (IVB) are such that measurement of the performance of a plurality of candidates can be carried out in-situ on the surface.

A fifth aspect of the present invention relates to a system for detecting a target substance in a media, comprising:

(VA) a substrate having a surface capable of forming thereon: (a1) a defined non-linearly spatially varying electric field; and (a2) a layer of marking molecules sensitive to the target substance, having a defined pattern in response to the defined non-linearly spatially varying electric field, said defined pattern defining a target area where the target substance can selectively bind; and (VB) a detecting device for detecting the presence and/or concentration of a target substance at the target area.

A sixth aspect of the present invention relates to a system for detecting the presence and/or concentration of a target substance in a media, comprising:

(VIA) an electrically conductive substrate having a surface capable of: (aa1) allowing a defined non-linearly spatially varying electric field to be established thereon; and (aa2) allowing the target substance to undergo an electrochemical reaction thereon in response to the defined non-linearly spatially varying electric field; and (VIB) a first device for detecting the occurrence of the electrochemical reaction.

In certain embodiments of the system according to the sixth aspect of the present invention, the system further comprises:

(VIC) a second device for determining the presence and/or concentration of the target substance in the media according to an algorithm correlating the location of the reaction to the presence and/or concentration of the target substance.

A seventh aspect of the present invention relates to an electrochemical method comprising:

(VII.1) providing an electrically conductive surface;

(VII.2) establishing a non-linearly spatially varying electric field on the surface; and (VII.3) implementing an electrochemical reaction to different degree on at least two differing locations of the surface having differing electric potential in response to the presence of the spatially varying electric field.

In certain embodiments of the method according to the seventh aspect of the present invention, in step (VII.2), the non-linearly spatially varying electric field is established by providing differing electric potential to at least three electrical contact points on the surface.

In certain embodiments of the method according to the seventh aspect of the present invention, in step (VII.3), multiple electrochemical reactions are implemented simultaneously on the surface.

In certain embodiments of the method according to the seventh aspect of the present invention, in step (VII.3), a plurality of candidate materials and/or processes are generated; and the process further comprises:

(VII.4A) measuring a plurality of candidates on the surface to yield performance data thereof;

(VII.5A) comparing the performance data of the measured candidates; and (VII.6A) discovering the target according to the comparison in step (VII.5).

In certain embodiments of the method according to the seventh aspect of the present invention, in step (VI.3), a defined pattern of a plurality of marking molecules is formed on the surface as a result of the electrochemical reaction, and the method further comprises the following steps:

(VII.4B) determining the target area on the surface where the target substance can selectively bind;

(VII.5B) contacting the media with the surface; and (VII.6B) binding the target substance to the surface and/or the marking molecules at the predetermined target area in the surface.

In certain embodiments of the method according to the seventh aspect of the present invention, in step (VII.3), a target substance, if any, undergoes an electrochemical reaction on the surface; and the method further comprises the following steps:

(VII.4C) determining the presence of the target substance by detecting the occurrence of the electrochemical reaction; and (VII.5C) optionally determining the concentration of the target substance in the media according to the location of the reaction.

Certain embodiments of the various aspects of the present invention have one or more of the following advantages. First, by using a non-linearly spatially varying electric field and electrochemical reactions responsive to such varying electric field, a large library of candidate materials and processes can be generated. Second, the large library can be effectively generated within a short period of time. Third, the large library enables detection of multiple species of target substances in a media, enabling efficient chemical and biological sensing processes and devices.

Additional embodiments of the invention will be set forth, in part, in the detailed description, and any claims which follow, and in part will be derived from the detailed description, or can be learned by practice of the invention. It is to be understood that both the foregoing general description and the following detailed description are exemplary and explanatory only and are not restrictive of the invention as disclosed.

BRIEF DESCRIPTION OF THE DRAWINGS

The accompanying drawings, which are incorporated in and constitute a part of this specification, illustrate certain embodiments of the instant invention and together with the description, serve to explain, without limitation, the principles of the invention.

DETAILED DESCRIPTION OF THE INVENTION

The following description of the invention is provided as an enabling teaching of the invention in its best, currently known embodiment. To this end, those skilled in the relevant art will recognize and appreciate that many changes can be made to the various embodiments of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

Unless otherwise indicated, all numbers such as those expressing weight percents of ingredients, dimensions, and values for certain physical properties such as electrical potential used in the specification and claims are to be understood as being modified in all instances by the term "about." It should also be understood that the precise numerical values used in the specification and claims form additional embodiments of the invention. Efforts have been made to ensure the accuracy of the numerical values disclosed in the Examples. Any measured numerical value, however, can inherently contain certain errors resulting from the standard deviation found in its respective measuring technique.

As used herein, the singular forms "a," "an" and "the" include plural referents unless the context clearly dictates otherwise. Thus, for example, reference to an "electrical contact point" includes embodiments having two or more such electrical contact points unless the context clearly indicates otherwise; and reference "a target substance" and "a candidate" includes embodiments having two or more target substances and candidates, respectively, unless the context clearly indicates otherwise.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, a "wt. %" or "weight percent" or "percent by weight" of a component, unless specifically stated to the contrary, is based on the total weight of the composition or article in which the component is included.

Certain electrochemical reactions can take place only when the electrical potential of the reactants is higher or lower than a threshold value. Beyond that threshold value, the reaction may be thermodynamically prohibited. Furthermore, the kinetics of certain electrochemical reactions can be controlled by the electrical potential of the reactants on the surface of an electrode. The controllability of the thermodynamics and kinetics of such electrochemical reactions can be exploited in many processes and devices the implantation of which involves such reactions. For example, the use of a field of linearly spatially variable electric potential in combinatorial catalyst discovery is known. However, the pool of useable variants generated by a field of linearly spatially variable electric potential is quite limited in number and functionality. Moreover, the use of a linearly variable electric potential field requires the use of a flat surface. Therefore, alternative approaches are desired in certain applications.

The present invention utilizes non-linearly spatially variable electric field to generate a non-linearly spatially variable electric potential gradient on a surface. The surface can be a flat surface or a curved surface, such as, e.g., a spherical or an ellipsoidal surface. The profile of the electric field can be controlled and can be precisely mapped such that at each location of the surface, the exact electric potential relative to a reference electrode (such as a AgCl/Ag reference electrode) can be determined before and during an electrochemical reaction is allowed to take place on the surface. An electrically conductive surface is typically employed to create the desired non-linearly spatially varying electric field. With knowledge of (i) the thermodynamic and kinetic behavior of a certain electrochemical reaction and (ii) the electrochemical potential profile on a given area of the surface, one can determine whether the electrochemical reaction would occur and the extent of such reaction in the area.

Figure 1:
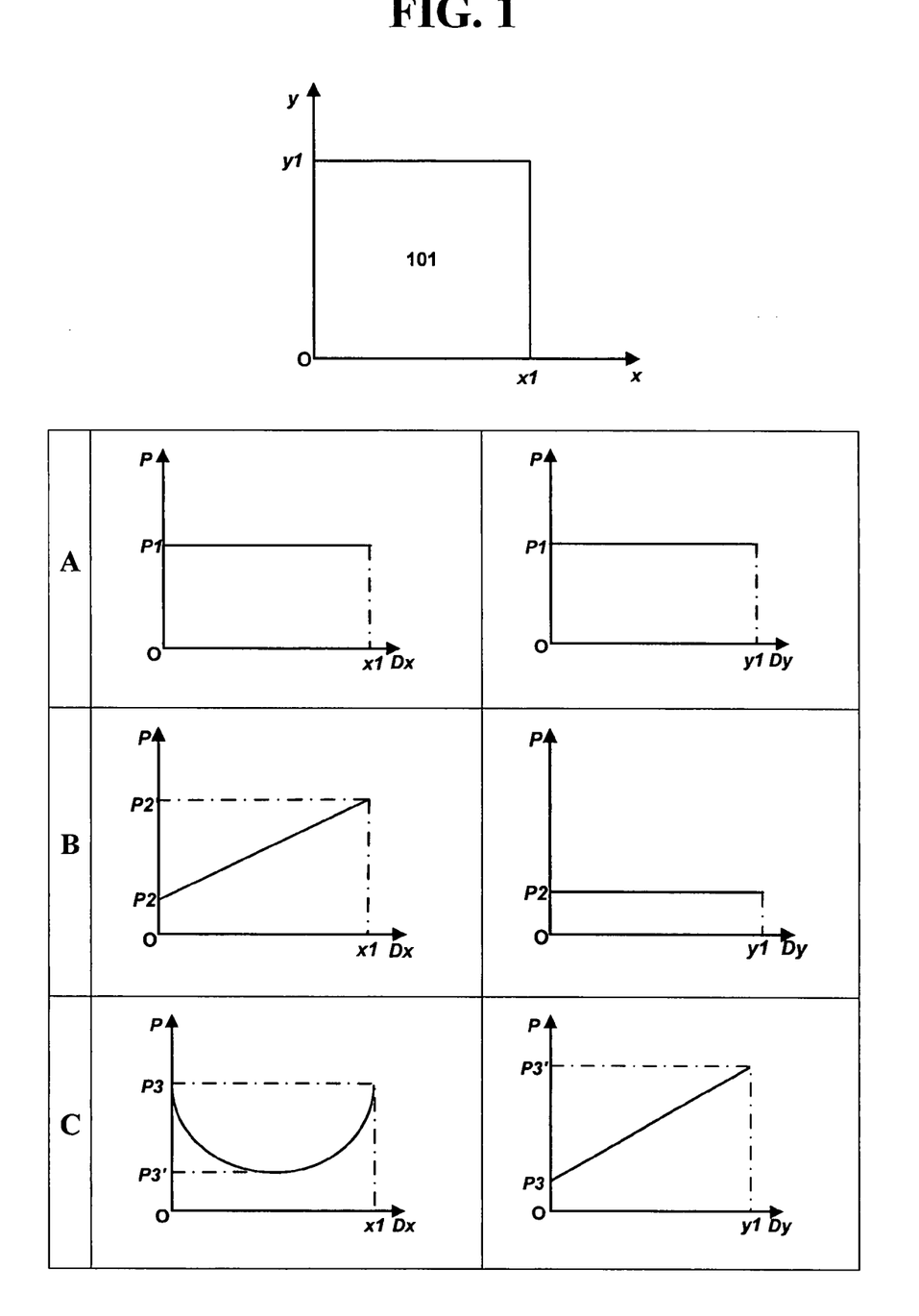
FIG. 1 shows schematic illustrations of various possible profiles of surface electrochemical potentials that can be applied to a flat conducting surface in certain embodiments of the present invention.

With reference to FIG. 1, schematic illustrations of various exemplary profiles of surface electrochemical potentials that can be applied to a conducting surface are shown. In FIG. 1, a flat substrate surface 101 having a length x1 a width y1 is shown. In all graph groups A, B, and C, Dx is the distance from point (0,0) on the surface 101 along the x axis, Dy is the distance from point (0,0) on the surface 101 along the y axis, and P is the electrochemical potential. In FIG. 1A, a constant potential P1 is applied to the entire surface, i.e., there is no spatial variation in the applied potential across the surface. In FIG. 1B, shown is a linear variation between two applied potentials P2 and P2', i.e., there is a variation in surface potential along one dimension or direction (x-direction in this example). FIG. 1C shows a non-linear or two dimensional spatial variation between two applied potentials P3 and P3', i.e., there is a variation in surface potential along two dimensions or directions (both x and y directions in this example).

In one embodiment, a conductive substrate can be provided having an array of "n" electrical potential contact points spatially arranged (e.g., in two dimensions in the case of a flat surface) on the first conductive surface, wherein "n" is at least 3. An electrical potential can then be applied to each of the "n" electrical contact points. By applying different electrical potentials to at least two of the "n" electrical potential contact points, a spatially varying surface potential can be provided wherein the spatial variance occurs in two dimensions, such as exemplified in FIG. 1C. Still further, this spatial variance can be controlled and even reproduced in a predetermined manner by selecting a desired scheme or program of electrical potential applications for each of the "n" electrical potential contact points.

The method of the present invention can be utilized in connection with any desired conductive substrate. However, in one embodiment it is preferred that the conductive substrate exhibit a surface resistance high enough to sustain the particular current densities that will be imposed due to the resulting electrochemical gradients. To that end, in an exemplary embodiment, a conducting substrate can be an indium tin oxide coated glass substrate (ITO) whose sheet resistance is approximately 100 ohms. Another example of such conductive surface would be a thin layer of gold having a thickness of not larger than 500 nm. The substrate can also optionally be coated with a conducting surface coating such as a conducting polymer. An exemplary conducting polymer can include polyaniline (PAni). The coating composition and thickness, if an optional coating is employed, can be uniform or can vary across the substrate surface. Similarly, the surface conductivity of the substrate and/or an optional coating material can be uniform or can vary across the substrate surface. Still further, the substrate can be a substantially uniform or continuous substrate or, alternatively, can be a patterned or pixelated substrate.

The surface of the conducting substrate can comprise any desired number "n" of electrical potential contact points. To that end, it will be appreciated that the desired number of contact points will depend, at least in part, upon the particular spatial variance in surface potential that is desired to be achieved. However, in one preferred embodiment, the surface of the conducting substrate comprises at least three electrical potential contact points. In various embodiments, the number ("n") of electrical contact points can be at least 3, at least 4, at least 5, at least 8, or more.

The contact points can be formed by attaching electrical leads to the surface of the conducting substrate. Any conductive wire or strip like material can be used as the electrical connection leads. However, if the method of the present invention is to be used in connection with an electrochemical system comprising a liquid electrolyte, it can be preferred for the lead material to be relatively inert or non-reactive in the particular electrolyte that is being used so as to reduce and/or prevent Faradaic current. To that end, suitable electrical lead material can include, without limitation, enameled conductive wires such as copper wires. The electrical leads can be attached to the surface of the substrate by using an electrically conductive paste or epoxy, or by soldering. Once attached, the conductive paste or epoxy, or soldering material can be covered with an insulating paste to isolate and insulate the individual contact points. Insulation of the lead wire in contact with an electrolyte in which the surface is at least partly immersed is desired for achieving the desired electrochemical potential profile on the surface.

Figure 2:
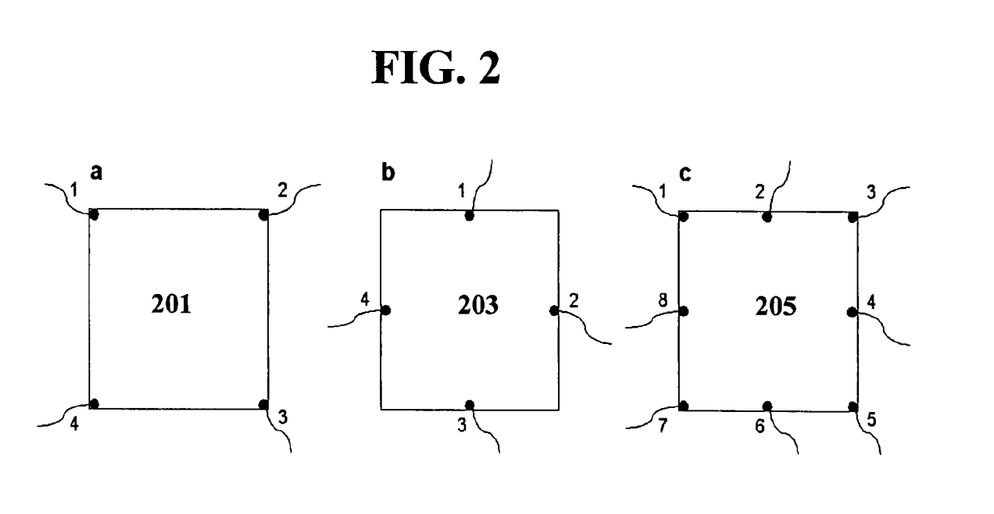
FIG. 2 shows schematic illustrations of several exemplary configurations for attaching lead wires (control points) to a substrate according to certain embodiments of the present invention.

Once the desired number "n" of contact points is determined, the contact points can be formed on the surface of the conducting substrate in any desired two dimensional spatial arrangements. To that end, it should again be appreciated that a desired spatial arrangement of the contact points will depend, at least in part, upon the desired two-dimensional spatial variation in surface potential to be achieved. With reference to FIG. 2, schematic illustrations of three exemplary spatial arrangements of electrical potential contact points comprised of lead wires attached to the surface of a conducting substrate 201, 203 and 203. For example, FIG. 2a shows an exemplary spatial arrangement of four electrical leads 1, 2, 3 and 4, positioned in the four corners of a conducting substrate. Alternatively, FIG. 2b shows an exemplary spatial arrangement of four electrical leads 1, 2, 3 and 4, positioned along each side edge of a conducting substrate. Still further, FIG. 2c shows a hybrid spatial arrangement of FIG. 2a and FIG. 2b comprised of eight electrical contact leads, wherein leads 1, 3, 5 and 7 are positioned in the four corners of a conducting substrate and leads 2, 4, 6 and 8, are positioned along each side edge of a conducting substrate.

Based upon the array of electrical contact points provided on the surface of the conducting substrate, a variety of possible surface potential spatial variation schemes can be obtained. The actual number of possible schemes will be dependent upon the number of electrical potential contact points present and the number of those contact points to which an electrical potential is actually applied. To that end, the number of possible spatial variation schemes "Q" can be calculated according to the equation $Q=n!/(n-r)!$; wherein "n" is the total number of electrical potential contact points and r is the subset of "n" to which an electrical potential is to be applied. In various exemplary embodiments, the number of electrical contact points to which an electrical potential is actually applied can be at least 2, at least 3, at least 4, or more.

For illustrative purposes and without intending to be limiting, exemplary calculations for a spatial array comprised of up to 8 electrical potential contact points such as that depicted in FIG. 2c are set forth in TABLE 1 below:

TABLE I

| r | n = 1 | n = 2 | n = 3 | n = 4 | n = 5 | n = 6 | n = 7 | n = 8 |
|---|---|---|---|---|---|---|---|---|
| 0 | 1 | 1 | 1 | 1 | 1 | 1 | 1 | 1 |
| 1 | 1 | 2 | 3 | 4 | 5 | 6 | 7 | 8 |
| 2 |   | 2 | 6 | 12 | 20 | 30 | 42 | 56 |
| 3 |   |   | 6 | 24 | 60 | 120 | 210 | 336 |
| 4 |   |   |   | 24 | 120 | 360 | 840 | 1680 |
| 5 |   |   |   |   | 120 | 720 | 2520 | 6720 |
| 6 |   |   |   |   |   | 720 | 5040 | 20160 |
| 7 |   |   |   |   |   |   | 5040 | 40320 |
| 8 |   |   |   |   |   |   |   | 40320 |
| Total | 2 | 5 | 16 | 65 | 326 | 1957 | 13700 | 109601 |

It can be seen from the exemplary calculations above that providing an array of eight electrical contact points on the surface of the substrate can generate more than 100,000 different potential gradient schemes or patterns on a given substrate. In other words, one can generate over 100,000 different combinations or schemes of electrical surface potential gradients on the surface of a single substrate. Further, it should be understood that these calculations only consider the possible permutations of the gradient schemes themselves, without reference to possible variations in the magnitude of each gradient within the given scheme. To that end, it should further be understood that the magnitude of each gradient within a given scheme is infinitely customizable by, for example, altering the magnitude of a given bias between any two electrical contact points.

Figure 3:
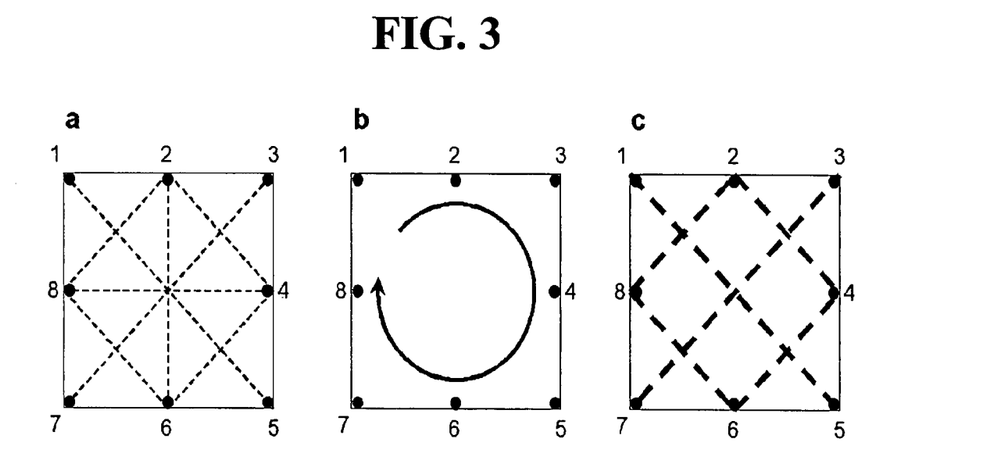
FIG. 3 shows schematic illustrations of exemplary configurations for applied potentials according to certain embodiments of the present invention.

With reference to FIG. 3, schematic illustrations of three exemplary gradient schemes that can be achieved with the array of eight electrical contact points depicted in FIG. 2c are shown. In particular, FIG. 3a schematically illustrates with dotted lines the possible combinations (including the possibilities of neighboring control points being at the same potential) where the control points at the ends of each dotted line are at the same potential. FIG. 3b illustrates an exemplary gradient scheme where all eight of the control points are maintained at unique and sequential potential values, thus forming a circular gradient scheme. Still further, FIG. 3c illustrates an exemplary scheme where control points 1, 3, 5 and 7 are maintained at the same potential E1, and points 2, 4, 6 and 8 are held at same potential, E2.

The actual control of each electrical contact or control point can be obtained by any conventionally known means for controlling the electrical potential applied to a lead. For example, in one embodiment, the potential applied to each of the leads forming the array of contact or control points can be controlled independently using a multi-channel potentiostat, wherein the potentiostat has at least a number of controllable channels "n" corresponding to the number "n" of control points provided on the surface of the conductive substrate.

The electrical potential applied to any two or more electrical contact points can be fixed or can vary over time. For example, the potential applied to one contact point can be fixed while the potential applied to a second contact point can vary. A varying applied potential can be useful in various applications where it is desirable to change either the nature of and/or the magnitude of the potential gradient across the surface of the conductive substrate. A varying potential can be applied using any conventional means or techniques, such as, for example, a voltammetric potential sweep generated by a conventional potentiostat. One of skill in the art could readily select an appropriate potential program and application technique for a specific application.

As discussed supra, electrochemical reactions are then allowed to take place on the surface in the presence of the non-linearly spatially varying electrical field. It is highly desired that the electrochemical reaction can be thermodynamically and/or kinetically controlled by the electrical potential applied to the reactants. Such controlled electrochemical reactions can find many applications to be described below.

I. Combinatorial Target Discovery Such as Catalyst Discovery

As will be appreciated by one of ordinary skill in the art, the discovery of catalysts is a challenging field. Although the rate of catalyst discovery has been greatly enhanced by the use of combinatorial methods in recent years, the methods of the present invention can further speed this discovery process immensely both in synthesis and screening steps. For example, a multi-component catalyst library could be created electrochemically on a substrate by co-depositing metal alloys from a solution containing the precursor metal ions. In view of the present invention, this can now be possible by exploiting the fact that different metals have different deposition potentials (and hence, rate). Thus, on a surface with non-uniform potential distribution, metal alloys with different composition can be deposited from the electrolyte in different positions or with different spatial relationships. Similarly, for a given catalyst library, the potential dependent catalytic activity can be mapped directly using the inventive control of nonlinear potential gradients.

In one embodiment of implementing the method of the first aspect of the present invention for catalyst discovery, one would first establish a non-linearly spatially varying surface (flat or curved), and then supply source materials such as metal salts on the surface. The electric field profile on the surface can be controlled in a way such that the metal salts undergo electro-deposition reactions at various locations of the surface at various degrees and/or speed. A result of such differential reactions at differing locations is the generation of a large library of candidate catalyst compositions across the surface. The compositions across the surface may have an essentially continuous gradient of at lease one component. Alternatively, it is also possible that the distribution of at least one component in the candidates is discontinuous. Where a continuous distribution profile of at least one component is achieved, it is possible to predict the concentration and/or presence of that particular component at a given location with knowledge of its concentration and/or presence and electric potential in the adjacent locations. With knowledge of the nature of the reactions and the electric field profile, one can predict the occurrence of certain reactions and the degrees and rates thereof.

The compositions can then be measured for their catalytic performance, desirably in-situ (meaning, maintaining the catalyst candidates on the surface without stripping it off). It is also possible to strip the compositions off the surface to conduct ex-situ performance measurement. In certain embodiments, during the process of measuring the performance of the catalyst, especially where the performance measurement can be conducted by using an electrochemical reaction responsive to the electrochemical potential to the reactants, it is desired that the performance test is conducted in the presence of an intentionally applied electrochemical potential profile, either the same as or different from the one used for the generation of the candidates. A target can be identified by comparing the measured performance data (catalyst performance data in the case of catalyst discovery such as reaction rate; ability to withstand adverse reaction condition; anti-toxicity ability, and the like). The composition of the target can be measured, in-situ or ex-situ, by using existing techniques, such as XPS, TOF-SIMS, Mass spectroscopy, wet chemical approaches, and the like. Composition analysis can be conducted only for the identified candidate having the desired performance, or can be conducted indiscriminately for all the candidates, provided the number of candidates and the measurement technique are not prohibitive.

Thus, a system for catalyst discovery and other material discovery applications according to the present invention could include: a substrate having an electrically conductive surface on which the desired electrical potential gradient can be established and the desired electrochemical reactions at desired degrees can occur to generate the candidates; a performance measuring device for quantifying the performance of the candidates, desirably in-situ; and optionally an analyzing device for determining the composition of at least the identified target candidate.

II. Chemical Sensors

It is contemplated certain embodiments of the methods of the present invention can have utility in the field of chemical sensors, such as, for example, a chemical sensor that can detect the presence and/or concentration of specific chemicals or class of chemicals in a media based on its response to an external stimulus. External stimuli can include a chemical reaction and the detected response can be any physically detectable property such as fluorescence, electric current, and the like. To that end, in an exemplary embodiment, it is contemplated that the inventive methods can for example be used to provide a pH based chemical sensor. For example, conductive substrate can be provided having a deposit that exhibits potential dependent pH variation. The control of non-linear gradients can be used to map the local variations in pH. In still another embodiment, it is contemplated that such chemical sensors can be used for screening libraries for combinatorial discovery of fuel cell anode catalysts. As proton exchange membrane fuel cell anodic reactions typically involve the release of protons, one could detect the local generation of protons using a fluorescent indicator in the presence of a non-linear gradient control to deduce the catalyst composition and corresponding reactivity relationships.

A typical chemical sensing process utilizing the invention of the present invention could include the following steps: providing an electrically conductive surface and establish a non-linearly spatially varying electric field (or electric potential gradient) on the surface; allowing the target substance to be detected to undergo electrochemical reactions differentially on the surface in response to the presence of the electric field, and detecting the presence and/or concentration of the target substance.

Take a pH-sensor as an example. A thin layer of Pt (less than 100 nm, e.g.) can be used as the electrically conductive surface. It is known that the occurrence of the following reaction:

$$2H^+ + e \rightarrow H_2$$

is dependent on the electrochemical potential of the $H^+$ ions at a given concentration of $H^+$ in the concentration. Therefore, the occurrence of the reaction at a certain location and/or the lack thereof at a certain location can be indicia of the concentration of the $H^+$ in the solution to be measured. By using detecting equipment such as a fluorescence detector which has capability to continuously monitor the surface reactions, continuous measurement of $H^+$ concentration of a stream is possible by using the pH sensor according to the present invention.

III. Electrochemical Biosensors

In still another embodiment, it is contemplated that the methods of the present invention will have utility in the field of electrochemical biosensors. Biosensors are analytical tools that can combine a biochemical recognition component (e.g., enzyme, antibody, DNA) with a physical transducer (e.g., electrochemical detectors such a pH electrode, surface modified electrodes, etc). Electrochemical biosensors can advantageously exhibit very high sensitivity with high accuracies. Electrochemical biosensors typically contain a single electrode with a single potential applied to detect change in a single parameter. However, by utilizing the methods of the present invention, the scope and capabilities of these sensors could be increased tremendously. For example a library of sensors could be prepared on a single substrate and a range of potentials could be applied using the methods of the present invention to simultaneously detect a plurality of target substances. For example, one contemplated surface is a layer of gold having a thickness of not more than 500 nm. It is known that thiol molecules can bind with the gold surface and the affinity thereof can be controlled via an electrochemical reaction. Therefore, by establishing a non-linearly spatially varying electrical field on the gold surface, a pattern of thiol molecules bound with the gold surface can be formed. Either the thiol molecule pattern and/or the pattern of the exposed gold surface can be used to bind molecules with a given dimension, geometry, and/or functional group on the molecule. Such binding yields detectable change at the given location of the surface. By detecting such change, one can determine the presence and/or concentration of the target substance to be detected.

As will be appreciated, the possible applications for the methods of the present invention are virtually endless and the above examples are merely provided for illustrative purposes and are not intended to limit the scope thereof

EXAMPLE

To further illustrate the principles of the present invention, the following examples are put forth so as to provide those of ordinary skill in the art with a complete disclosure and description of how the methods claimed herein can be performed and evaluated. They are intended to be purely exemplary of the invention and are not intended to limit the scope of what the inventors regard as their invention. Efforts have been made to ensure accuracy with respect to numbers (e.g., amounts, temperatures, etc.); however, some errors and deviations may have occurred. Unless indicated otherwise, parts are parts by weight, temperature is ° C. or is at ambient temperature, and pressure is at or near atmospheric.

In the following examples, a model system was prepared comprising an indium tin oxide coated glass substrate further coated with a polyaniline conducting polymer (PAni). The PAni was chosen for illustration of this invention as it exhibits a potential dependent conductivity and consequently a potential dependent coloration. To that end, the three principal oxidation states of PAni are: 1) Leucoemaraldine, which is the fully reduced state and is identifiable by a greenish yellow color; 2) Emaraldine, which is the half or partially oxidized state and is identifiable by a green color; and 3) Pernigraniline, which is the fully oxidized state and is identifiable by a deep blue color. Further, PAni can be reversibly switched between these oxidation states by switching the surface potentials. Hence, a surface electrochemical gradient on a polyaniline coated substrate will exhibit localized variations in color depending on the applied potential program.

Four enameled copper wire electrical leads were attached to the corners of an indium tin oxide (ITO) coated glass substrate surface using a conductive silver epoxy. The exposed regions of the copper wire and the silver epoxy were covered with regular epoxy to insulate them from the electrolyte. Polyaniline (PAni) was electrochemically deposited onto an indium tin oxide (ITO) coated glass substrate from an electrolyte solution containing 0.1 M aniline and 0.5 M sulfuric acid. This was achieved by cycling the ITO substrate between −0.2 V and +1.15 V against an Ag/AgCl reference electrode at a scan rate of about 20 mV·s$^{-1}$ for two cycles. Following deposition, the substrate was rinsed thoroughly in deionized water and then subjected to electrochemical cleaning. The electrochemical cleaning further included cycling the PAni—coated substrate between—0.2 V and 0.6 V against an Ag/AgCl reference electrode for five cycles.

The substrate was subsequently rinsed thoroughly in deionized water and immersed in a 0.5M sulfuric acid solution for further experimentation. Chronoamperometry was used to maintain constant potentials at varying points on the substrate. Chronoamperometry is an electrochemical technique wherein a constant potential can be applied to a given electrode and current can be monitored as a function of time. In particular, a computer controlled eight-channel multi-potentiostat, commercially available from CH Instruments Inc., of Austin, Tex., was used for performing the chronoamperometry experiments. Further, a remote controlled digital camera was also used to capture pictures of the substrate while the various potential programs were applied. The visual results of various chronoamperometry experiments are can be clearly observed from the images of the substrate.

Figure 4:
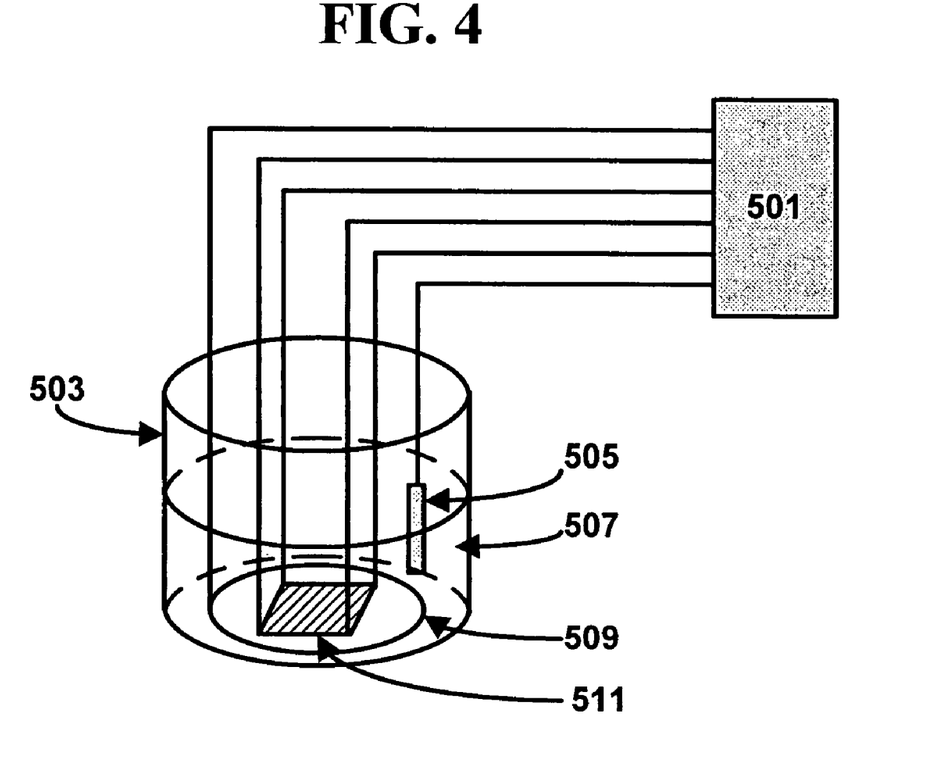
FIG. 4 is a schematic illustration of the apparatus set-up of the experiments described infra.

FIG. 4 schematically illustrates the apparatus set-up of the experiments. As shown in this figure, a substrate 511 as prepared above was immersed in electrolyte 507 placed in a beaker 503. A circular counter electrode 509 made of platinum is placed around the substrate 511. Placed in the electrolyte is also an AgCl/Ag reference electrode 505. All the electrical leads to the four corners of the substrate 511, the counter electrode 509 and the reference electrode 505 are connected to the output leads of a multi-potentiostat.

Figure 5:
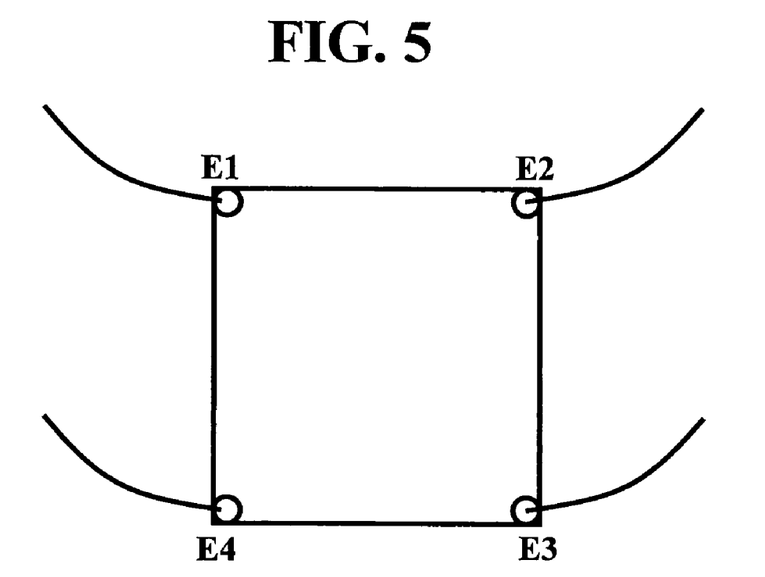
FIG. 5 is a schematic illustration of an exemplary PAni coated ITO substrate according to one embodiment of the present invention. The substrate further comprised four electrical contact or control points (E1, E2, E3 and E4).

With reference to FIG. 5, a schematic illustration of a PAni coated ITO substrate with four contact points (E1, E2, E3 and E4) is shown. The four contact points are formed by enameled copper wires attached at four corners of the substrate using a conductive silver epoxy. The color of the PAni was light green at open circuit condition.

The PAni coated ITO substrate depicted in FIG. 5 was first subjected to five different but uniform surface potentials wherein contact points E1, E2, E3 and E4 are equivalent. In Experiment No. 1, the uniform potential was at zero volts. In Experiment No. 2, the uniform potential was 0.2V. In Experiment No. 3, the uniform potential was 0.4 V. In Experiment No. 4, the uniform potential was at 0.6 V. In Experiment No. 5, the uniform potential was 0.8 V. In all experiments, the color shade of the full substrate was essentially uniform. Colors of the substrate in all experiments are provided in TABLE II below. The color shading corresponds to the varying oxidation states of PAni described above.

TABLE II

| | Experiment No. | | | | |
|---|---|---|---|---|---|
| | 1 | 2 | 3 | 4 | 5 |
| Uniform Surface Potential (V) | 0 | 0.2 | 0.4 | 0.6 | 0.8 |
| Color of Substrate | greenish-yellow | light green | dark green | blue | dark blue |

In Experiment Nos. 6-9, the PAni coated ITO substrate of FIG. 5 was then subjected to four separate linear potential gradients in 0.5M sulfuric acid. In these pictures, the potentials of E3 and E4 were held constant and the potentials of E1 and E2 were varied systematically from Experiment Nos. 6-9. Further, potential E1 was equal to E2 in each of the experiments. In Experiment No. 6, potentials E1 and E2 were set at 0.4 V and potentials E3 and E4 were set at −0.2 V. In Experiment No. 7, potentials E1 and E2 were set at 0.6 V and potentials E3 and E4 were again set at −0.2 V. In Experiment No. 8, potentials E1 and E2 were set at 0.8 V and potentials E3 and E4 were again set at −0.2 V. In Experiment No. 9, potentials E1 and E2 were set at 1.0 V and potentials E3 and E4 were again set at −0.2 V.

In Experiment Nos. 10 and 11, the PAni coated ITO substrate of FIG. 5 was subjected to two non-linearly or two-dimensionally spatially varying potential gradients in 0.5 M sulfuric acid. In Experiment No. 10, potential E1 was 0.4 V, potential E2 was 0 V, potential E3 was 0.4 V, and potential E4 was 0 V. In Experiment No. 11, potential E1 was −0.2 V, potential E2 was 0.8 V, potential E3 was −0.2 V, and potential E4 was 0.8 V. A position dependent variation in the color of the PAni film can be observed on the substrate surface. Notably, the color change radially from the points of contact as would be the expected variation in potentials under such an exemplary two dimensional potential gradient.

Color and shading of certain points of the substrate in Experiment Nos. 6-11 are provided in TABLE III below.

TABLE III

| | | Experiment No. | | | | | |
|---|---|---|---|---|---|---|---|
| | | 6 | 7 | 8 | 9 | 10 | 11 |
| Potential (V) | E1 | 0.4 | 0.6 | 0.8 | 1.0 | 0.4 | −0.2 |
| | E2 | 0.4 | 0.6 | 0.8 | 1.0 | 0 | 0.8 |
| | E3 | −0.2 | −0.2 | −0.2 | −0.2 | 0.4 | −0.2 |
| | E4 | −0.2 | −0.2 | −0.2 | −0.2 | 0 | 0.8 |
| Color Shading | E1 Corner | Dark green | Light blue | Dark blue | Dark Blue | Dark green | Greenish yellow |
| | E2 Corner | Dark green | Light blue | Dark Blue | Dark blue | Greenish-yellow | Dark blue |
| | E3 | Greenish- | Greenish- | Greenish- | Greenish- | Dark | Greenish- |

TABLE III-continued

| | Experiment No. | | | | | |
|---|---|---|---|---|---|---|
| | 6 | 7 | 8 | 9 | 10 | 11 |
| Corner | yellow | yellow | yellow | yellow | green | yellow |
| E4 Corner | Greenish-yellow | Greenish-yellow | Greenish-yellow | Greenish-yellow | Greenish-yellow | Dark blue |
| Substrate Center | Greenish-yellow | Light Green | Light Blue | Blue | Greenish-yellow | Green |

Lastly, it should also be understood that while the present invention has been described in detail with respect to certain illustrative and specific embodiments thereof, it should not be considered limited to such, as numerous modifications are possible without departing from the broad scope of the present invention as defined in the appended claims.

What is claimed is:

1. A method for selecting a target from a plurality of candidates of materials and/or processes, comprising:
   (I.1) providing a single electrically conductive surface;
   (I.2) providing a defined non-linearly spatially varying electric field across the single electrically conductive surface;
   (I.3) supplying a source material to the single electrically conductive surface;
   (I.4) causing the source material to undergo an electrochemical process on the single electrically conductive surface in the presence of the non-linearly spatially varying electric field, whereby a plurality of candidates are generated;
   (I.5) measuring a plurality of candidates on the single electrically conductive surface to yield performance data thereof;
   (I.6) and selecting the target based on the data in step (I.5).

2. A method according to claim 1, wherein in step (I.5), at least part of the measuring is conducted in-situ while the candidates remain on the surface.

3. A method according to claim 1, wherein in step (I.4), at least 100 candidates are generated; and in step (I.5), at least 100 candidates are measured.

4. A method according to claim 1, wherein step (I.5) is at least partly carried out on the surface in the presence of an electric field.

5. A method according to claim 1, wherein:
   in step (I.3), the source material is a metal precursor;
   in step (I.4), the metal precursor is reduced to elemental metal and deposited on the surface to form the plurality of candidate material; and
   in step (I.5), the catalytic performance of the candidates is measured.

6. A method according to claim 5, further comprising a step (I.7) below:
   (I.7) analyzing the composition of the target.

7. A method according to claim 1, wherein in step (I.3), a plurality of candidate materials are generated, said candidate materials having an essentially continuous gradient of at least one component thereof across the surface.

8. A method for detecting a target substance in a media, comprising:
   (II.1) providing an electrically conductive single surface having thereon a layer of marking molecules sensitive to the target substance;
   (II.2) forming a defined pattern of the marking molecules by providing a defined non-linearly spatially varying electric field across the single surface;
   (II.3) determining the target area on the single surface where the target substance can selectively bind;
   (II.4) contacting the media with the single surface; and
   (II.5) binding the target substance to the single surface and/or the marking molecules at the predetermined target area in the single surface.

9. A method according to claim 8, wherein in step (II.1), the surface comprises a self-assembled mono-layer of thiol molecules.

10. A method according to claim 8, further comprising:
    (II.6) determining the presence or absence of the target substance at the predetermined target area on the surface.

11. A method according to claim 8, wherein:
    in step (II.2), the defined pattern of the marking molecules defines target areas where multiple target substances can separately, simultaneously, selectively bind.

12. A method for detecting the presence and/or concentration of a target substance in a media, comprising:
    (III.1) providing a single electrically conductive surface;
    (III.2) providing a defined non-linearly spatially varying electric field across the single electrically conductive surface;
    (III.3) contacting the media with the single electrically conductive surface;
    (III.4) causing the target substance, if any, to undergo an electrochemical reaction on the single electrically conductive surface in the presence of the electric field; and
    (III.5) determining the presence of the target substance by detecting the occurrence of the electrochemical reaction; and
    (III.6) optionally determining the concentration of the target substance in the media according to the location of the reaction.

13. A method according to claim 12, further comprising the following step (III.7):
    (III.7) correlating the location of the electrochemical reaction to the presence and/or concentration of a target substance in the media.

14. An electrochemical method, comprising:
    (VII.1) providing a single electrically conductive surface;
    (VII.2) establishing a non-linearly spatially varying electric field on the single electrically conductive surface; and
    (VII.3) implementing an electrochemical reaction to different degree on at least two differing locations of the single electrically conductive surface having differing electric potential in response to the presence of the spatially varying electric field.

15. A method according to claim 14, wherein in step (VII.2), the non-linearly spatially varying electric field is established by providing differing electric potential to at least three electrical contact points on the surface.

16. A method according to claim 14, wherein in step (VII.3), multiple electrochemical reactions are implemented simultaneously on the surface.

17. A method according to claim 14, wherein in step (VII.3), a plurality of candidate materials and/or processes are generated; and the process further comprises:

(VII.4A) measuring a plurality of candidates on the surface to yield performance data thereof;

(VII.5A) and selecting the target based on the data in step (VII.4A).

18. A method according to claim 14, wherein in step (VI.3), a defined pattern of a plurality of marking molecules is formed on the surface as a result of the electrochemical reaction, and the process further comprises the following steps:

(VII.4B) determining the target area on the surface where the target substance can selectively bind;

(VII.5B) contacting the media with the surface; and (VII.6B) binding the target substance to the surface and/or the marking molecules at the predetermined target area in the surface.

19. A method according to claim 14, wherein in step (VII.3), a target substance, if any, undergoes an electrochemical reaction on the surface; and the process further comprises the following steps:

(VII.4C) determining the presence of the target substance by detecting the occurrence of the electrochemical reaction; and (VII.5C) optionally determining the concentration of the target substance in the media according to the location of the reaction.

* * * * *